(12) United States Patent
Ishii et al.

(10) Patent No.: US 8,524,913 B2
(45) Date of Patent: Sep. 3, 2013

(54) PROCESS FOR PRODUCTION OF α-TRIFLUOROMETHYL-β-SUBSTITUTED-β-AMINO ACID

(75) Inventors: Akihiro Ishii, Kawagoe (JP); Manabu Yasumoto, Kawagoe (JP); Takako Yamazaki, Kawagoe (JP); Kaori Mogi, Kawagoe (JP); Takashi Masuda, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 117 days.

(21) Appl. No.: 13/002,595

(22) PCT Filed: Aug. 27, 2009

(86) PCT No.: PCT/JP2009/064971
§ 371 (c)(1),
(2), (4) Date: Jan. 4, 2011

(87) PCT Pub. No.: WO2010/026918
PCT Pub. Date: Mar. 11, 2010

(65) Prior Publication Data
US 2011/0152536 A1    Jun. 23, 2011

(30) Foreign Application Priority Data

Sep. 3, 2008 (JP) .................... 2008-225448
Dec. 5, 2008 (JP) .................... 2008-311446

(51) Int. Cl.
*C07D 261/04* (2006.01)
*C07C 229/20* (2006.01)

(52) U.S. Cl.
USPC .......................... 548/243; 562/574

(58) Field of Classification Search
None
See application file for complete search history.

(56) References Cited

U.S. PATENT DOCUMENTS
2007/0010579 A1   1/2007   Gusmeroli

FOREIGN PATENT DOCUMENTS

| JP | 2002-138070 A | 5/2002 |
|----|----|----|
| JP | 2007-502314 A | 2/2007 |
| WO | WO 2004/103074 A1 | 12/2004 |
| WO | WO 2005/016866 A2 | 2/2005 |
| WO | WO 2005/016866 A3 | 2/2005 |
| WO | WO 2008/020007 A2 | 2/2008 |

OTHER PUBLICATIONS

Deqiang Niu et al., "Concerted Conjugate Addition of Nucleophiles to Alkenoates. Part I: Mechanism of N-Alkylhydroxylamine Additions", J. Am. Chem. Soc., 1999, pp. 2456-2459, vol. 121, No. 11, American Chemical Society.
European Search Report dated Sep. 9, 2011 (Six (6) pages).
International Search Report with English translation dated Oct. 6, 2009 (four (4) pages).
Pang et al., Transition metal-catalyzed formation of CF3-substituted alpha, beta-unsaturated alkene and the synthesis of alpha-trifluoromethyl substituted beta-amino ester, Tetrahedron, 2006, pp. 11760-11765, vol. 62.
Shimada et al., First highly stereoselective synthesis of anti-alpha-trifluoromethyl-beta-amino acid derivatives, Chemical Communications, 2006, pp. 3628-3630.
Avenoza et al., A Convenient Enantioselective Synthesis of (S)-a-Trifluoromethylisoserine, Journal of Organic Chemistry, 2005, pp. 5721-5724, vol. 70.
PCT/ISA/237 (foreign language) (three (3) pages).

*Primary Examiner* — Kamal Saeed
(74) *Attorney, Agent, or Firm* — Crowell & Moring LLP

(57) ABSTRACT

α-Trifluoromethyl-β-substituted-β-amino acids can be produced by allowing α-trifluoromethyl-β-substituted-α,β-unsaturated esters to react with hydroxylamine to convert α-trifluoromethyl-β-substituted-α,β-unsaturated esters into dehydrogenated closed-ring body of α-trifluoromethyl-β-substituted-β-amino acid, and by hydrogenolyzing the dehydrogenated closed-ring body. According to this production process, novel α-trifluoromethyl-β-substituted-β-amino acids which are free amino acids whose functional groups are not protected can be produced, in which β-position substituent is not limited to aromatic ring group or substituted aromatic ring group while the relative stereochemistry of α-position and β-position can be also controlled.

4 Claims, No Drawings

PROCESS FOR PRODUCTION OF α-TRIFLUOROMETHYL-β-SUBSTITUTED-β-AMINO ACID

TECHNICAL FIELD

This invention relates to a production process for α-trifluoromethyl-β-substituted-β-amino acids which are important as intermediates of drugs and medicines.

BACKGROUND OF INVENTION

α-Trifluoromethyl-β-substituted-β-amino acids are important as intermediates of drugs and medicines. As conventional production processes, there are (1) a process of allowing α-trifluoromethyl-β-substituted-α,β-unsaturated esters to react with hydrogen azide ($HN_3$) (see Non-patent Citation 1), (2) a process for allowing derivative of 2-bromo-3,3,3-trifluoropropanoic acid to react with imines (see Non-Patent Citation 2), and the like.

While many synthesis examples for β-position non-substituted body by reaction of derivative of α-trifluoromethyl acrylic acid and nitrogen nucleophile have been reported, production process for β-position substituted body has been extremely limited.

PRIOR ART CITATIONS

Non-Patent Citations

Non-patent Citation 1: Tetrahedron (Great Britain), 2006, Volume 62, p. 11760-11765
Non-patent Citation 2: Chemical Communications (Great Britain), 2006, p. 3628-3630

SUMMARY OF INVENTION

An object of the present invention is to provide practical production methods for α-trifluoromethyl-β-substituted-β-amino acids. For this purpose, it is required to solve the problems in conventional techniques.

For Non-patent Citation 1, it is required to avoid use of hydrogen azide which is explosive and toxic. For Non-patent Citation 2, it is required to improve atomic economy. Further, in these Non-patent Citations, β-position substituent is limited to aromatic ring group or substituted aromatic ring group.

Additionally, in production of amino acids like the present invention, it is eagerly required to produce free amino acid [$N_2N$—$CO_2H$] in which protective groups for amino group and carboxyl group are freely selectable according to use. In order to design a synthesis process (including a de-protection step for functional group) of α-trifluoromethyl-β-substituted-β-amino acids which are free amino acids and objects of the present invention, it is required to sufficiently take account of side-reactions (epimerization, de-hydrogen fluoride, de-ammonia, and the like) due to a high acid degree of α-position proton. Actually it has been reported that hydrolysis of a product obtained by Reformatsky reaction to carboxyl group cannot easily proceed (see Non-patent Citation 2).

Lastly a control of stereochemistry to α-position trifluoromethyl group becomes an important problem for β-position substituted body.

The present inventors have made eager studies in view of the above-mentioned problems. As a result, it has been found that α-trifluoromethyl-β-substituted-β-amino acids can be produced by allowing α-trifluoromethyl-β-substituted-α,β-unsaturated esters to react with hydroxylamine to convert α-trifluoromethyl-β-substituted-α,β-unsaturated esters into dehydrogenated closed-ring body of α-trifluoromethyl-β-substituted-β-amino acids (a first step), and by hydrogenolyzing the dehydrogenated closed-ring body (a second step). According to this production process, free amino acid which has substituent at β-position and whose functional group is not protected can be produced. Additionally, β-position substituent is not limited to aromatic ring group or substituted aromatic ring group. Further, it has become apparent that a relative configuration of α-trifluoromethyl-β-substituted-β-amino acids as object products can be controlled even if a stereochemistry of double bond of α-trifluoromethyl-β-substituted-α,β-unsaturated esters as raw material substrates is a mixture of E-body and Z-body (the relative configuration can be highly controlled particularly in case that β-position substituent is alkyl group or substituted alkyl group).

Dehydrogenated closed-ring body of α-trifluoromethyl-β-substituted-β-amino acids obtained at the first step are novel compounds, and it can be easily converted into α-trifluoromethyl-β-substituted-β-amino acids by hydrogenolysis, and therefore it is a very useful precursor of the amino acids. Additionally, α-trifluoromethyl-β-substituted-β-amino acids corresponding to free amino acids obtained by the present invention are also novel compounds and very important not only as intermediates of drugs and medicines but also as analog of natural β-amino acids having biological activity.

In other words, the present invention includes [Invention 1] to [Invention 6] and provides practical production processes for α-trifluoromethyl-β-substituted-β-amino acids.

[Invention 1] A process of producing α-trifluoromethyl-β-substituted-β-amino acids represented by a general formula [4]

[chem. 4]

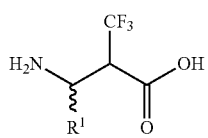

[4]

by allowing α-trifluoromethyl-β-substituted-α,β-unsaturated esters represented by a general formula [1]

[chem. 1]

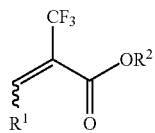

[1]

to react with hydroxylamine represented by a general formula [2] [chem.2]

   [2]

to convert α-trifluoromethyl-β-substituted-α,β-unsaturated esters into dehydrogenated closed-ring body of α-trifluoromethyl-β-substituted-β-amino acid represented by a general formula [3]

[chem. 3]

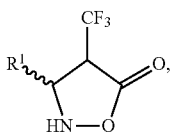
[3]

and by hydrogenolyzing the dehydrogenated closed-ring body, Wherein, in the formulae, $R^1$ is alkyl group, substituted alkyl group, aromatic ring group, substituted aromatic ring group, alkoxycarbonyl group or substituted alkoxycarbonyl group, and $R^2$ is alkyl group or substituted alkyl group; a wavy line in the general formula [1] indicates that stereochemistry of double bond is E-body, Z-body or a mixture of E-body and Z-body; and a wavy line in the general formula [3] and in the general formula [4] indicates that stereochemistry of $R^1$ to trifluoromethyl group is syn-body, anti-body, or a mixture of syn-body and anti-body.

[Invention 2] A process of producing α-trifluoromethyl-β-substituted-β-amino acids represented by a general formula [7]

[chem. 8]

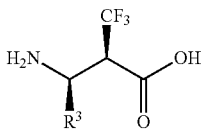
[7]

by allowing α-trifluoromethyl-β-substituted-α,β-unsaturated esters represented by a general formula [5]

[chem. 5]

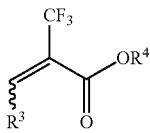
[5]

to react with hydroxylamine represented by a general formula [2] [chem.6]

 [2]

to convert α-trifluoromethyl-β-substituted-α,β-unsaturated esters into dehydrogenated closed-ring body of α-trifluoromethyl-β-substituted-β-amino acid represented by a general formula [6]

[chem. 7]

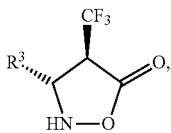
[6]

and by hydrogenolyzing the dehydrogenated closed-ring body, Wherein, in the formulae, $R^3$ is alkyl group or substituted alkyl group, and $R^4$ is alkyl group; a wavy line in the general formula [5] indicates that stereochemistry of double bond is E-body, Z-body or a mixture of E-body and Z-body; representation of relative configuration in the general formula [6] indicates that stereochemistry of $R^3$ to trifluoromethyl group is anti-body; and representation of relative configuration in the general formula [7] indicates that stereochemistry of $R^3$ to trifluoromethyl group is syn-body.

[Invention 3] A dehydrogenated closed-ring body of α-trifluoromethyl-β-substituted-β-amino acid, represented by a general formula [3]

[chem. 9]

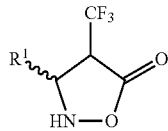
[3]

where $R^1$ is alkyl group, substituted alkyl group, aromatic ring group, substituted aromatic ring group, alkoxycarbonyl group or substituted alkoxycarbonyl group; and a wavy line indicates that stereochemistry of $R^1$ to trifluoromethyl group is syn-body, anti-body, or a mixture of syn-body and anti-body.

[Invention 4] A dehydrogenated closed-ring body of α-trifluoromethyl-β-substituted-β-amino acid represented by a general formula [6]

[chem. 10]

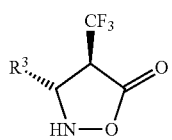
[6]

where $R^3$ is alkyl group or substituted alkyl group; and representation of relative configuration indicates that stereochemistry of $R^3$ to trifluoromethyl group is anti-body.

[Invention 5] α-Trifluoromethyl-β-substituted-β-amino acids represented by a general formula [4]

[chem. 11]

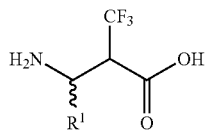
[4]

where $R^1$ is alkyl group, substituted alkyl group, aromatic ring group, substituted aromatic ring group, alkoxycarbonyl group or substituted alkoxycarbonyl group; and a wavy line indicates that stereochemistry of $R^1$ to trifluoromethyl group is syn-body, anti-body, or a mixture of syn-body and anti-body.

[Invention 6] α-Trifluoromethyl-β-substituted-β-amino acids represented by a general formula [7]

[chem. 12]

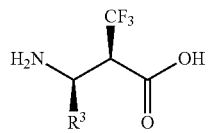

[7]

where $R^3$ is alkyl group or substituted alkyl group; and representation of relative configuration indicates that stereochemistry of $R^3$ to trifluoromethyl group is syn-body.

DETAILED DESCRIPTION

Advantageous points of the present invention over prior art will be discussed hereinafter.

According to the production process of the present invention, it is not required to use explosive and toxic reaction agents, and atomic economy is extremely high. Additionally, according to the present production process, novel α-trifluoromethyl-β-substituted-β-amino acids which are free amino acids whose functional groups are not protected can be produced; β-position substituent cannot be also limited to aromatic ring group or substituted aromatic ring group; and relative stereochemistry of α-position and β-position can be also controlled.

Thus, the production process of the present invention is a production process which not only solves all problems of prior art but also is easily industrially carried out because of being simple in operation and high in productivity while hardly by-producing impurities which are difficult to be separated.

Detailed discussion will be made on production process of α-trifluoromethyl-β-substituted-β-amino acids, according to the present invention.

The present invention is a process of producing α-trifluoromethyl-β-substituted-β-amino acids represented by the general formula [4] by allowing α-trifluoromethyl-β-substituted-α,β-unsaturated esters represented by a general formula [1] to react with hydroxylamine represented by the general formula [2] to convert α-trifluoromethyl-β-substituted-α,β-unsaturated esters into dehydrogenated closed-ring body of α-trifluoromethyl-β-substituted-β-amino acid represented by the general formula [3] (the first step), and by hydrogenolyzing the dehydrogenated closed-ring body (the second step).

(1) First Step $R^1$ of α-trifluoromethyl-β-substituted-α,β-unsaturated esters represented by the general formula [1] is alkyl group, substituted alkyl group, aromatic ring group, substituted aromatic ring group, alkoxycarbonyl group or substituted alkoxycarbonyl group. Of these, alkyl group and substituted alkyl group are preferable, and particularly alkyl group is more preferable.

Alkyl group has a carbon number of from 1 to 18 and can take linear or branched chain structure or cyclic structure (in case that the carbon number is not less than 3). Aromatic ring group has a carbon number of from 1 to 18 and can be aromatic hydrocarbon group such as phenyl group, naphthyl group, anthryl group or the like, or aromatic heterocycle group containing heteroatom such as nitrogen atom, oxygen atom, sulfur atom or the like, for example, pyrrolyl group, furyl group, thienyl group, indolyl group, benzofuryl group, benzothienyl group or the like. Alkyl group (R) of alkoxycarbonyl group ($-CO_2R$) is the same as the above-mentioned alkyl group.

The alkyl group, aromatic ring group and alkoxycarbonyl group may have an arbitrary number of substituents on arbitrary atoms and in an arbitrary combination (corresponding to substituted alkyl group, substituted aromatic ring group and substituted alkoxycarbonyl group, respectively). Examples of such substituents are halogen atom such as fluorine, chlorine, bromine and/or iodine; azide group; nitro group; lower alkyl group such as methyl group, ethyl group, propyl group and/or the like; lower haloalkyl group such as fluoromethyl group, chloromethyl group, bromomethyl group and/or the like; lower alkoxy group such as methoxy group, ethoxy group, propoxy group and/or the like; lower haloalkoxy group such as fluoromethoxy group, chloromethoxy group, bromomethoxy group and/or the like; lower alkylamino group such as dimethylamino group, diethylamino group, dipropylamino group and/or the like; lower alkylthio group such as methylthio group, ethylthio group, propylthio group and/or the like; cyano group; lower alkoxycarbonyl group such as methoxycarbonyl group, ethoxycarbonyl group, propoxycarbonyl group and/or the like; aminocarbonyl group ($CONH_2$); lower aminocarbonyl group such as dimethylaminocarbonyl group, diethylaminocarbonyl group, dipropylaminocarbonyl group and/or the like; unsaturated group such as alkenyl group, alkynyl group and/or the like; aromatic ring group such as phenyl group, naphthyl group, pyrrolyl group, furyl group, thienyl group and/or the like; aromatic ring oxy group such as phenoxy group, naphthoxy group, pyrrolyloxy group, furyloxy group, thienyloxy group and/or the like; aliphatic heterocycle group such as piperidyl group, piperidino group, morpholinyl group and/or the like; hydroxyl group; protected hydroxyl group; amino group (including amino acid or peptide residue group); protected amino group; thiol group; protected thiol group; aldehyde group; protected aldehyde group; carboxyl group; protected carboxyl group; and/or the like. In the present specification, the following terms are used to mean matters mentioned below: "lower" means linear or branched chain structure having carbon number of from 1 to 6, or cyclic structure (in case that carbon number is not less than 3) having carbon number of from 1 to 6. In case that "unsaturated group" is double bond (alkenyl group), either geometrical isomerism of E-body or Z-body can be taken. As "protective groups for hydroxyl group, amino group, thiol group, aldehyde group and carboxyl group", protective groups or the like described in Protective Groups in Organic Synthesis, Third Edition, 1999, John Wiley & Sons, Inc. may be used (two or more functional groups may be protected by one protective group). Additionally, to "unsaturated group", "aromatic ring group", "aromatic ring oxy group" and "aliphatic heterocycle group", substitution of halogen atom, azide group, nitro group, lower alkyl group, lower haloalkyl group, lower alkoxy group, lower haloalkoxy group, lower alkylamino group, lower alkylthio group, cyano group, lower alkoxycarbonyl group, aminocarbonyl group, lower alkylaminocarbonyl group, hydroxyl group, protected hydroxyl group, amino group, protected amino group, thiol group, protected thiol group, aldehyde group, protected aldehyde group, carboxyl group, protected carboxyl group, and/or the like can be made. These substituents include one serving as nucleophilic agent in the first step and one which is reduced in the second step, in which desired reaction in each step can be selectively accomplished by employing preferable reaction condition.

R² of α-trifluoromethyl-β-substituted-α,β-unsaturated esters represented by the general formula [1] is alkyl group or substituted alkyl group. Of these, alkyl group is preferable, and particularly methyl group and ethyl group are more preferable.

Alkyl group and substituted alkyl group are the same as alkyl group and substituted alkyl group of the above-mentioned R¹.

A wavy line in α-trifluoromethyl-β-substituted-α,β-unsaturated esters represented by the general formula [1] indicates that stereochemistry of double bond is E-body, Z-body or a mixture of E-body and Z-body.

α-Trifluoromethyl-β-substituted-α,β-unsaturated esters represented by the general formula [1] can be produced with reference to Journal of Fluorine Chemistry (Holland), 2002, Volume 113, p. 177-183 and Tetrahedron Letters (Great Britain), 2001, Volume 42, p. 5929-5931, and the like.

A used amount of hydroxylamine represented by the formula [2] is preferably not less than 0.7 mole, usually preferably 0.8 to 10 moles, and particularly more preferably 0.9 to 5 moles, relative to 1 mole of α-trifluoromethyl-β-substituted-α,β-unsaturated esters represented by the general formula [1].

As hydroxylamine represented by the formula [2], its aqueous solution, its polymer-carried body, its salt (hydrochloric acid salt, sulfuric acid salt, phosphoric acid salt, nitric acid salt and the like) formed with acid, and the like can be used in addition to hydroxylamine itself. In case of using the salt produced with acid, a method in which hydroxylamine is made free in the presence of base in a reaction system to be provided to reaction is convenient.

Examples of such base are organic base such as triethylamine, diisopropylethylamine, tri-n-propylamine, tri-n-butylamine, pyridine, 2,4-lutidine, 2,6-lutidine, 3,5-lutidine, 2,4,6-collidine and the like, and inorganic base such as sodium hydrogencarbonate, potassium hydrogencarbonate, sodium carbonate, potassium carbonate, sodium hydroxide, potassium hydroxide and the like. Of these, triethylamine, diisopropylethylamine, pyridine, 2,6-lutidine, 2,4,6-collidine, sodium carbonate, potassium carbonate, sodium hydroxide and potassium hydroxide are preferable, and particularly triethylamine, diisopropylethylamine, pyridine, 2,6-lutidine, sodium carbonate and potassium carbonate are more preferable.

A used amount of such base is not less than 0.7 mole, usually preferably 0.8 to 10 moles, particularly more preferably 0.9 to 5 moles, relative to 1 mole of hydroxylamine contained in salt produced with acid.

Examples of the reaction solvent are aliphatic hydrocarbon family such as n-hexane, cyclohexane, n-heptane and the like; aromatic hydrocarbon family such as benzene, toluene, xylene and the like; halogenated hydrocarbon family such as methylene chloride, chloroform, 1,2-dichloroethane and the like; ether family such as diethyl ether, tetrahydrofuran, diisopropyl ether, tert-butylmethyl ether and the like; ester family such as ethyl acetate, n-butyl acetate and the like; nitrile family such as acetonitrile, propionitrile and the like; amide family such as N,N-dimethylformamide, N,N-dimethylacetamide, 1,3-dimethyl-2-imidazolidinone and the like; dimethylsulfoxide; alcohol family such as methanol, ethanol, n-propanol, isopropanol, n-butanol and the like; water; and the like. Of these, n-hexane, n-heptane, toluene, xylene, methylene chloride, tetrahydrofuran, diisopropyl ether, tert-butylmethyl ether, ethyl acetate, acetonitrile, propionitrile, N,N-dimethylformamide, dimethylsulfoxide, methanol, ethanol, n-propanol and isopropanol are preferable, and particularly n-heptane, toluene, methylene chloride, tetrahydrofuran, ethyl acetate, acetonitrile, N,N-dimethylformamide, methanol, ethanol and isopropanol are more preferable. These reaction solvents may be used singly or in combination. Additionally, for the present invention, reaction can be made by using no solvent.

A used amount of the reaction solvent is not less than 0.01 L (liter), usually preferably 0.03 to 10 L, particularly more preferably 0.05 to 7 L, relative to 1 mole of α-trifluoromethyl-β-substituted-α,β-unsaturated esters represented by the general formula [1].

A temperature condition is sufficient to be within a range of from −30 to +120° C., and usually preferably from −20 to +110° C. and particularly more preferably from −10 to +100° C.

A reaction time is sufficient to be within a range of not longer than 72 hours, and different according to raw material substrate and reaction condition. Therefore, it is preferable to track the progressing status of a reaction by using analytical means such as gas chromatography, liquid chromatography, nuclear magnetic resonance or the like and to determine a time at which the raw material substrate is almost diminished, as a terminal point.

An after-treatment is made as follows: A reaction-terminated liquid (the reaction solvent is concentrated if necessary) is diluted with an organic solvent (for example, n-hexane, n-heptane, toluene, xylene, methylene chloride, diisopropyl ether, tert-butylmethyl ether, ethyl acetate or the like), and washed with water or an aqueous solution of an inorganic base of alkali metal (for example, sodium hydrogencarbonate, potassium hydrogencarbonate, sodium carbonate, potassium carbonate or the like) (dried over a drying agent such as anhydrous sodium sulfate, anhydrous magnesium sulfate or the like if necessary), followed by concentrating a recovered organic layer, so that dehydrogenated closed-ring body of α-trifluoromethyl-β-substituted-β-amino acid represented by a general formula [3] can be obtained as a crude product. A wavy line in the general formula [3] indicates that the stereochemistry of R¹ to trifluoromethyl group is syn-body, anti-body, or a mixture of syn-body and anti-body. Particularly in case that β-position substituent is alkyl group or substituted alkyl group, a relative configuration can be controlled to anti-body at a high level [not less than 90% de (diastereomer excess)]. The crude product can be purified to a high chemical purity by activated carbon treatment, distillation, recrystallization, column chromatography and/or the like, if necessary. According to column chromatography, minor diastereomer can be also isolated.

In the present invention, the second step can be continuously carried out without carrying out the after-treatment at the first step. Specifically, hydrogenolyzing can be carried out by adding a transition metal catalyst into a reaction-terminated liquid at the first step (adding the reaction solvent at the second step if necessary), and putting the liquid in an atmosphere of hydrogen gas ($H_2$). An object of the present invention is to provide a practical production process for α-trifluoromethyl-β-substituted-β-amino acids. From such a viewpoint, it can be said that the above-mentioned one-pot reaction is a preferable mode.

The stereochemistry of dehydrogenated closed-ring body of α-trifluoromethyl-β-substituted-β-amino acid represented by the general formula [6] is the same as that of compound represented by a general formula [8] because of representing a relative configuration.

[chem. 13]

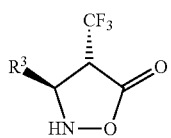

[8]

(2) Second Step

The second step is accomplished by allowing dehydrogenated closed-ring body of α-trifluoromethyl-β-substituted-β-amino acid represented by the general formula [3] to react with hydrogen gas ($H_2$) in the presence of a transition metal catalyst.

Examples of the transition metal catalyst are platinum catalyst such as platinum black, platinum/activated carbon, platinum/graphite, platinum/alumina, platinum/zirconia, platinum oxide and the like; nickel catalyst such as reduced nickel, Raney nickel, Raney nickel sponge, Raney nickel provided with platinum, and the like; iridium catalyst such as iridium black, iridium/calcium carbonate, iridium oxide and the like; palladium catalyst such as palladium black, palladium sponge, palladium/activated carbon, palladium/alumina, palladium/calcium carbonate, palladium/strontium carbonate, palladium/barium sulfate, palladium hydroxide, palladium acetate, palladium chloride and the like; and the like. Of these, palladium catalyst is preferable, and particularly palladium/activated carbon, palladium/alumina, palladium/calcium carbonate, palladium/barium sulfate and palladium hydroxide are more preferable. These transition metal catalysts may be used singly or in combination. A carried amount of transition metal in case of using a catalyst in which transition metal is carried on a carrier is sufficient to be from 0.1 to 50 wt %, and usually preferably from 0.5 to 40 wt %, particularly more preferably from 1 to 30 wt %. Additionally, transition metal catalyst may be used in the form of hydrated product. Further, transition metal catalyst preserved in water or inactive liquid may be used in order to improve safety for treatment and in order to prevent a metal surface from oxidation.

A used amount of transition metal catalyst is sufficient to be a catalytic amount, and usually preferably from 0.00001 to 0.5 mole, particularly more preferably from 0.0001 to 0.3 mole, relative to 1 mole of dehydrogenated closed-ring body of α-trifluoromethyl-β-substituted-β-amino acid represented by the general formula [3].

A used amount of hydrogen gas is sufficient to be not less than 1 mole, and usually preferably an excessive amount, particularly more preferably an excessive amount under a pressured condition, relative 1 mole of dehydrogenated closed-ring body of α-trifluoromethyl-β-substituted-β-amino acid represented by the general formula [3].

Such pressured condition for hydrogen gas is sufficient to be within a range of not higher than 5 MPa, usually preferably from 0.01 to 4 MPa, particularly more preferably from 0.03 to 3 MPa.

Examples of the reaction solvent are aromatic hydrocarbon family such as benzene, toluene, xylene and the like; ether family such as diethyl ether, tetrahydrofuran, diisopropyl ether, tert-butyl methyl ether and the like; ester family such as ethyl acetate, n-butyl acetate and the like; alcohol family such as methanol, ethanol, n-propanol, isopropanol, n-butanol and the like; water; and the like. Of these, toluene, xylene, tetrahydrofuran, diisopropyl ether, tert-butyl methyl ether, ethyl acetate, methanol, ethanol, n-propanol and isopropanol are preferable, and particularly toluene, tetrahydrofuran, ethyl acetate, methanol, ethanol and isopropanol are more preferable. These reaction solvents may be used singly or in combination. Additionally, for the present invention, reaction can be made by using no solvent.

A used amount of the reaction solvent is sufficient to be not less than 0.01 L, and usually preferably from 0.03 to 20 L, particularly more preferably from 0.05 to 10 L, relative to 1 mole of dehydrogenated closed-ring body of α-trifluoromethyl-β-substituted-β-amino acid represented by the general formula [3].

A temperature condition is sufficient to be within a range of from −30 to +150° C., and usually preferably from −20 to +125° C. and particularly more preferably from −10 to +100° C.

A reaction time is sufficient to be within a range of not longer than 48 hours, and different according to raw material substrate and reaction condition. Therefore, it is preferable to track the progressing status of a reaction by using analytical means such as gas chromatography, liquid chromatography, nuclear magnetic resonance or the like and to determine a time at which the raw material substrate is almost diminished, as a terminal point.

An after-treatment is made as follows: The transition metal catalyst remaining in a reaction-terminated liquid is filtered, and then a filtrate is concentrated, thereby making it possible to obtain α-trifluoromethyl-β-substituted-β-amino acid represented by the general formula [4] as a crude product. A wavy line in the general formula [4] indicates that the stereochemistry of $R^1$ to trifluoromethyl group is syn-body, anti-body, or a mixture of syn-body and anti-body. Particularly in case that β-position substituent is alkyl group or substituted alkyl group, a relative configuration can be controlled to syn-body at a high level [not less than 90% de (diastereomer excess)]. The crude product can be purified to a high chemical purity by activated carbon treatment, distillation, recrystallization, column chromatography and/or the like, if necessary. According to column chromatography, minor diastereomer can be also isolated. Additionally, isolation can be made upon conversion to "salt formed with acid" or "salt formed with base", and purification to a further high chemical purity can be made by recrystallization or the like of the salt if necessary.

Examples of such acid are inorganic acid such as hydrochloric acid, hydrobromic acid, sulfuric acid, nitric acid and the like, and organic acid such as maleic acid, fumaric acid, phthalic acid, methanesulfonic acid, benzenesulfonic acid, p-toluenesulfonic acid, malic acid, tartaric acid, mandelic acid and the like (arbitrary optically active body can be used in case that optical isomers exist, if necessary).

Examples of such base are inorganic base such as lithium hydroxide, sodium hydroxide, potassium hydroxide, calcium hydroxide and the like, and organic base such as triethylamine, diisopropylethylamine, dicyclohexylamine, cis- or trans-1,2-diaminocyclohexane (arbitrary optically active body can be used in case that optical isomers exist, if necessary) and the like.

The stereochemistry of α-trifluoromethyl-β-substituted-β-amino acids represented by the general formula [7] is the same as that of compound represented by a general formula [9] because of representing a relative configuration.

[chem. 14]

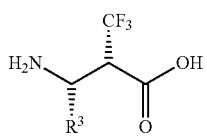

[9]

α-Trifluoromethyl-β-substituted-β-amino acids represented by the general formula [7] are obtained from dehydrogenated closed-ring body of α-trifluoromethyl-β-substituted-β-amino acid represented by the general formula [6], while α-trifluoromethyl-β-substituted-β-amino acids represented by the general formula [9] are obtained from dehydrogenated closed-ring body of α-trifluoromethyl-β-substituted-β-amino acid represented by the general formula [8].

According to the present invention, α-trifluoromethyl-β-substituted-β-amino acids can be produced by allowing α-trifluoromethyl-β-substituted-α,β-unsaturated esters to react with hydroxylamine to convert α-trifluoromethyl-β-substituted-α,β-unsaturated esters into dehydrogenated closed-ring body of α-trifluoromethyl-β-substituted-β-amino acid and by hydrogenolyzing the dehydrogenated closed-ring body (Mode 1)

Concerning the raw material substrate, it is more preferable that substituent at β-position is alkyl group or substituted alkyl group, and ester group is alkyl ester. The raw material substrate is readily available, featuring that desired reaction effectively proceeds and that the relative configuration of obtained α-trifluoromethyl-β-substituted-β-amino acids can be also controlled at a high level (Mode 2).

Dehydrogenated closed-ring body of α-trifluoromethyl-β-substituted-β-amino acid, obtained in Mode 1 is novel compound and can be easily converted to α-trifluoromethyl-β-substituted-β-amino acids under hydrogenolysis so as to be very useful precursor of the amino acids (Mode 3).

In Mode 3, a case that substituent at 0-position is alkyl group or substituted alkyl group is more preferable mode (Mode 4).

α-Trifluoromethyl-β-substituted-β-amino acids as free amino acids, obtained in Mode 1 are also novel compounds and very important not only as intermediates of drugs and medicines but also as analog of natural β-amino acid having biological activity (Mode 5).

In Mode 5, a case that substituent at β-position is alkyl group or substituted alkyl group is more preferable mode (Mode 6).

EXAMPLES

Modes carrying out the invention will be specifically discussed with reference to Examples, in which the present invention is not limited to these Examples.

Example 1

To 500 mg (2.379 mmol, 1.00 eq) of α-trifluoromethyl-β-substituted-α,β-unsaturated esters (E-body Z-body=44:56) represented by the following formula:

[chem. 15]

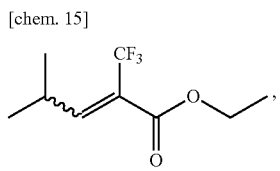

5 mL of methanol, 563 mg (5.564 mmol, 2.34 eq) of triethylamine and 333 mg (4.792 mmol, 2.01 eq) of hydrochloric acid salt of hydroxylamine represented by the following formula:

  [chem.16]

were added, and then stirring was made at room temperature for 2 hours. A conversion rate was 99% according to gas chromatography of a reaction-terminated liquid. The reaction-terminated liquid was diluted with 30 mL of ethyl acetate, and washing was made two times with 30 mL of water. A recovered organic layer was dried over anhydrous magnesium sulfate, concentrated under reduced pressure, and dried under vacuum, thereby obtaining 300 mg of dehydrogenated closed-ring body of α-trifluoromethyl-β-substituted-β-amino acid represented by the following formula:

[chem. 17]

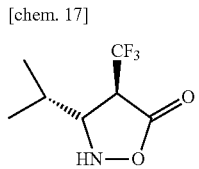

A yield was 64%. A gas chromatography purity (an analytical value at the time of measuring the conversion rate of the reaction-terminated liquid) was 90.8%. A product was single diastereomer according to $^1$H-NMR and $^{19}$F-NMR (a relative configuration was determined to be anti-body according to a single crystal X-ray structural analysis which will be discussed after)

Results of $^1$H-NMR and $^{19}$F-NMR of α-trifluoromethyl-β-substituted-α,β-unsaturated esters and dehydrogenated closed-ring body of α-trifluoromethyl-β-substituted-β-amino acid are shown below.

α-Trifluoromethyl-β-substituted-α,β-unsaturated esters (gas chromatography purity: 97.5%):

$^1$H-NMR (reference material: $(CH_3)_4$Si, deuterated solvent: $CDCl_3$), δ ppm: 1.09 (m, 6H), 1.33 (m, 3H), 3.08 (Z-body, m, 1H in total), 3.29 (E-body, m, 1H in total), 4.29 (m, 2H), 6.56 (E-body, d, 10.2 Hz, 1H in total), 6.97 (Z-body, d, 11.0 Hz, 1H in total); and $^{19}$F-NMR (reference material: $C_6F_6$, deuterated solvent: $CDCl_3$), δ ppm: 97.80 (E-body, s, 3F in total), 103.05 (Z-body, s, 3F in total).

Dehydrogenated closed-ring body of α-trifluoromethyl-β-substituted-1-amino acid:

$^1$H-NMR (reference material: (CH$_3$)$_4$Si, deuterated solvent: CDCl$_3$), δ ppm: 1.03 (d, 7.2 Hz, 3H), 1.05 (d, 7.2 Hz, 3H), 1.99 (m, 1H), 3.31 (dq, 4.2 Hz, 9.2 Hz, 1H), 3.74 (m, 1H), 7.10 (br, 1 H); and $^{19}$F-NMR (reference material: C$_6$F$_6$, deuterated solvent: CDCl$_3$), δ ppm: 94.35 (s, 3F).

A HR-MS of dehydrogenated closed-ring body of α-trifluoromethyl-β-substituted-β-amino acid is shown below.

Obsd. m/z: 198.073 (Calc. Mass: 198.074, Error (ppm): −1.4, Assignment: C$_7$H$_{11}$NO$_2$F$_3^+$, Calc. Structure: [M+H]+).

To 100 mg (0.507 mmol, 1.00 eq) of dehydrogenated closed-ring body of ortrifluoromethyl-β-substituted-β-amino acid represented by the above formula, 3 mL of methanol and 2.4 mg (50% hydrated product, 0.00056 mmol, 0.001 eq) of 5% palladium/activated carbon were added, and the pressure of hydrogen gas (H$_2$) was set at 0.6 MPa, followed by making stirring over night at room temperature. A conversion rate was 92% according to gas chromatography of the reaction-terminated liquid. The reaction-terminated liquid was Celite-filtered, and the filtrate was concentrated under vacuum and dried under reduced pressure, thereby obtaining 109 mg of α-trifluoromethyl-β-substituted-β-amino acids represented by the following formula:

[chem. 18]

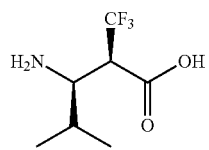

A yield was quantitative. The product was single diastereomer according to $^1$H-NMR and $^{19}$F-NMR.

An excessive amount of concentrated hydrochloric acid was added, and concentration under vacuum and drying under reduced pressure were made, thereby obtaining HCl salt of α-trifluoromethyl-β-substituted-β-amino acids as crystal. According to the single crystal X-ray structural analysis, the relative configuration of α-position and β-position was syn-body.

To 40 mL of methanol, 4.52 g (19.2 mmol) of the hydrochloric acid salt similarly produced and 3.65 g (19.2 mmol, 1.00 eq) of p-toluenesulfonic acid monohydrate were added. Dissolving under heating was made at 40 to 50° C., and methanol was concentrated under reduced pressure. Then, 27 mL of isopropanol and 6 mL of n-heptane were added to the residue, and dissolving under heating was made at 90° C., followed by gradually lowering the temperature to room temperature. Precipitated crystal was filtered and washed with a small amount of n-heptane, followed by being dried under vacuum, thereby obtaining 6.12 g of p-toluenesulfonic acid salt of α-trifluoromethyl-β-substituted-β-amino acids. The recovery was 86%. The diastereomer ratio was syn-body: anti-body=>98:2 according to $^1$H-NMR and $^{19}$F-NMR analyses.

Results of $^1$H-NMR and $^{19}$F-NMR of α-trifluoromethyl-β-substituted-β-amino acids, the HCl salt and the p-toluenesulfonic acid salt are shown below.

α-Trifluoromethyl-β-substituted-β-amino acids:

$^1$H-NMR (reference material: internal lock, deuterated solvent: D$_2$O), δ ppm: 0.90 (d, 6.8 Hz, 3H), 0.94 (d, 6.8 Hz, 3H), 2.00 (m, 1H), 3.29 (m, 1H), 3.46 (m, 1H); and $^{19}$F-NMR (reference material: CF$_3$SO$_3$K, deuterated solvent: D$_2$O), δ ppm: 12.33 (d, 9.4 Hz, 3F).

HCl salt of α-trifluoromethyl-β-substituted-β-amino acids:

$^1$H-NMR (reference material: internal lock, deuterated solvent: D$_2$O), δ ppm: 0.90 (d, 6.8 Hz, 3H), 0.93 (d, 6.8 Hz, 3H), 2.00 (m, 1H), 3.53 (m, 2H); and $^{19}$F-NMR (reference material: CF$_3$SO$_3$K, deuterated solvent: D$_2$O), δ ppm: 12.51 (d, 12.0 Hz, 3F).

p-Toluenesulfonic acid salt of α-trifluoromethyl-β-substituted-β-amino acids:

$^1$H-NMR (reference material: internal lock, deuterated solvent: D$_2$O), δ ppm: 0.92 (d, 7.0 Hz, 3H), 0.95 (d, 7.0 Hz, 3H), 2.02 (m, 1H), 2.27 (s, 3H), 3.43-3.54 (m, 2H), 7.24 (d, 8.3 Hz, 2H), 7.56 (d, 8.3 Hz, 2H)/NH$_2$, CO$_2$H and SO3H could not be identified; and $^{19}$F-NMR (reference material: CF$_3$SO$_3$K, deuterated solvent: D$_2$O), δ ppm: 12.43 (d, 9.0 Hz, 3F).

A HR-MS of α-trifluoromethyl-β-substituted-β-amino acids is shown below.

Obsd. m/z: 200.089 (Calc. Mass: 200.089, Error (ppm): −0.6, Assignment: C$_7$H$_{13}$NO$_2$F$_3^+$, Calc. Structure: [M+H]+).

Example 2

To 45 mL of methanol, 7.70 g (42.3 mmol, 1.00 eq) of α-trifluoromethyl-β-substituted-α,β-unsaturated esters (E-body:Z-body=61:39) represented by the following formula:

[chem. 19]

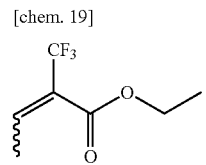

was added, and cooling was made by an ice bath. Then, 2.79 g (42.2 mmol, 1.00 eq) of 50% aqueous solution of hydroxylamine represented by the following formula:

H$_2$N—OH    [chem.20]

was added, and stirring was made at 20° C. over night. Further, stirring was made at 30 to 35° C. for 3 hours and 30 minutes. According to $^1$H- and $^{19}$F-NMR analyses of the reaction mixture liquid, it was confirmed that dehydrogenated closed-ring body of α-trifluoromethyl-β-substituted-β-amino acid represented by the following formula:

[chem. 21]

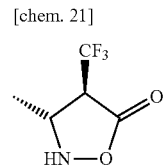

was quantitatively produced as single diastereomer (>95:5) (the relative configuration of major diastereomer was determined to be anti-body from the similarity to Example 1).

Results of $^1$H- and $^{19}$F-NMR of α-trifluoromethyl-β-substituted-α,β-unsaturated esters and dehydrogenated closed-ring body of α-trifluoromethyl-β-substituted-β-amino acid are shown below.

α-Trifluoromethyl-β-substituted-α,β-unsaturated esters:

$^1$H-NMR (reference material: (CH$_3$)$_4$Si, deuterated solvent: CDCl$_3$), δ ppm: 1.33 (m, 3H), 2.09 (Z-body, m, 3H in total), 2.17 (E-body, m, 3H in total), 4.29 (m, 2H), 6.95 (E-body, m, 1H in total), 7.33 (Z-body, m, 1H in total); and $^{19}$F-NMR (reference material: C$_6$H$_6$, deuterated solvent: CDCl$_3$), δ ppm: 97.62 (E-body, s, 3F in total), 102.98 (Z-body, s, 3F in total).

Dehydrogenated closed-ring body of α-trifluoromethyl-β-substituted-β-amino acid:

$^1$H-NMR (reference material: (CH$_3$)$_4$Si, deuterated solvent; CDCl$_3$), δ ppm: 1.47 (d, 6.4 Hz, 3H), 3.19 (m, 1H), 4.14 (m, 1H)/NH could not be identified; and $^{19}$F-NMR (reference material: C$_6$H$_6$, deuterated solvent: CDCl$_3$), δ ppm: 94.42 (d, 6.0 Hz, 3F).

To the reaction-terminated liquid (prepared to be 42.3 mmol) of dehydrogenated closed-ring body of α-trifluoromethyl-β-substituted-β-amino acid represented by the above formula, 40 mL of methanol and 900 mg (50% hydrated product, 0.211 mmol, 0.005 eq) of 5% palladium/activated carbon were added, and the pressure of hydrogen gas (H$_2$) was set at 0.5 MPa, followed by stirring at room temperature for 2 hours and 30 minutes. According to $^1$H- and $^{19}$F-NMR analyses of the reaction mixture liquid, it was confirmed that α-trifluoromethyl-β-substituted-β-amino acids represented by the following formula:

[chem. 22]

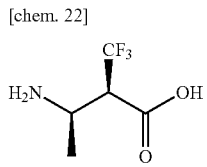

was quantitatively produced as single diastereomer (>95:5) (the relative configuration of major diastereomer was determined to be syn-body from the similarity to Example 1). To the reaction-terminated liquid (prepared to be 42.3 mmol) of α-trifluoromethyl-β-substituted-β-amino acids represented by the above formula, 4 mL (48.7 mmol, 1.15 eq) of 37% hydrochloric acid and 6 mL of water were added, and Celite-filtration was made. The residue was washed with a small amount of methanol, and concentration under reduced pressure and drying under vacuum were made. Further, azeotropic dehydration with 10 mL of toluene was made thereby obtaining 8.00 g of hydrochloric acid salt of α-trifluoromethyl-β-substituted-β-amino acids represented by the above-mentioned formula.

To 15 mL of methanol, 1.30 g (prepared to be 6.87 mmol) of the hydrochloric acid salt and 1.36 g (7.15 mmol, 1.04 eq) of p-toluenesulfonic acid monohydrate were added, and dissolving under heating was made at 40 to 50° C., followed by making concentration of almost whole methanol (about 13 mL) under reduced. The precipitated crystal was filtered, and washed with a small amount of n-heptane, followed by being subjected to drying under vacuum, thereby obtaining 960 mg of p-toluenesulfonic acid salt (refined product) of α-trifluoromethyl-β-substituted-β-amino acids represented by the above-mentioned formula. The total yield from α-trifluoromethyl-β-substituted-α,β-unsaturated esters was 41%. The diastereomer ratio was syn-body:anti-body=>98:2 according to $^1$H- and $^{19}$F-NMR analyses.

Results of $^1$H-NMR and $^{19}$F-NMR of hydrochloric acid salt and p-toluenesulfonic acid salt of α-trifluoromethyl-β-substituted-β-amino acids are shown below.

Hydrochloric acid salt of α-trifluoromethyl-β-substituted-β-amino acids:

$^1$H-NMR (reference material: internal lock, deuterated solvent: D$_2$O), δ ppm: 1.35 (d, 6.8 Hz, 3H), 3.50 (m, 1H), 3.89 (m, 1H)/NH$_2$, CO$_2$H and HCl could not identified; and $^{19}$F-NMR (reference material: CF$_3$SO$_3$K, deuterated solvent: D$_2$O), δ ppm: 13.59 (d, 9.0 Hz, 3F).

p-Toluenesulfonic acid salt of α-trifluoromethyl-β-substituted-β-amino acids:

$^1$H-NMR (reference material: internal lock, deuterated solvent: D$_2$O), δ ppm: 1.36 (d, 6.8 Hz, 3H), 2.28 (s, 3H), 3.46 (m, 1H), 3.89 (m, 1H), 7.25 (d, 8.4 Hz, 2H), 7.57 (d, 8.4 Hz, 2H)/NH$_2$, CO$_2$H and SO$_3$H could not be identified; and $^{19}$F-NMR (reference material: CF$_3$SO$_3$K, deuterated solvent: D$_2$O), δ ppm: 13.50 (d, 9.0 Hz, 3F).

Example 3

To 70 mL of methanol, 16.0 g (76.1 mmol, 1.00 eq) of α-trifluoromethyl-β-substituted-α,β-unsaturated esters (E-body:Z-body=55:45) represented by the following formula:

[chem. 23]

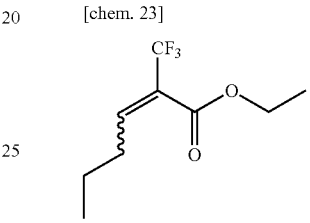

was added, and cooling was made by an ice bath. Then, 5.03 g (76.1 mmol, 1.00 eq) of 50% aqueous solution of hydroxylamine represented by the following formula:

H$_2$N—OH [chem.24]

was added, and stirring was made at room temperature for 1 day. Further, stirring was made at 35° C. for 6 hours. According to $^1$H- and $^{19}$F-NMR analyses of the reaction mixture liquid, it was confirmed that dehydrogenated closed-ring body of α-trifluoromethyl-β-substituted-β-amino acid represented by the following formula:

[chem. 25]

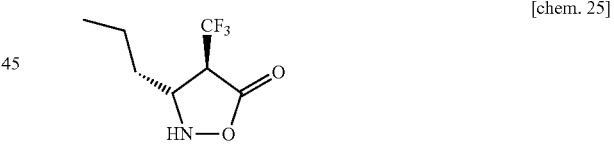

was quantitatively produced as single diastereomer (>95:5) (the relative configuration of major diastereomer was determined to be anti-body from the similarity to Example 1).

Results of $^1$H- and $^{19}$F-NMR of α-trifluoromethyl-β-substituted-α,β-unsaturated esters and dehydrogenated closed-ring body of α-trifluoromethyl-β-substituted-β-amino acid are shown below.

α-Trifluoromethyl-β-substituted-a,13-unsaturated esters:

$^1$H-NMR (reference material: (CH$_3$)$_4$Si, deuterated solvent: CDCl$_3$), δ ppm: 0.97 (m, 3H), 1.33 (m, 3H), 1.54 (m, 2H), 2.46 (Z-body, m, 2H in total), 2.57 (E-body, m, 2H in total), 4.29 (m, 2H), 6.82 (E-body, m, 1H in total), 7.20 (Z-body, m, 1H in total); and $^{19}$F-NMR (reference material: C$_6$H$_6$, deuterated solvent: CDCl$_3$), δ ppm: 97.77 (E-body, s, 3F in total), 103.08 (Z-body, s, 3F in total).

Dehydrogenated closed-ring body of α-trifluoromethyl-β-substituted-β-amino acid:

$^1$H-NMR (reference material: $(CH_3)_4Si$, deuterated solvent: $CDCl_3$), δ ppm: 0.99 (t, 7.2 Hz, 3H), 1.25-1.90 (m, 4H), 3.21 (m, 1H), 4.01 (m, 1H)/NH could not be identified; and $^{19}$F-NMR (reference material: $C_6H_6$, deuterated solvent: $CDCl_3$), δ ppm: 94.54 (d, 9.0 Hz, 3F).

To the reaction-terminated liquid (prepared to be 76.1 mmol) of dehydrogenated closed-ring body of α-trifluoromethyl-β-substituted-β-amino acid represented by the above formula, 80 mL of methanol and 3.24 g (50% hydrated product, 0.761 mmol, 0.01 eq) of 5% palladium/activated carbon were added, and the pressure of hydrogen gas ($H_2$) was set at 0.5 MPa, followed by stirring at room temperature for 2 hours and 30 minutes. According to $^1$H- and $^{19}$F-NMR analyses of the reaction mixture liquid, it was confirmed that α-trifluoromethyl-β-substituted-β-amino acids represented by the following formula:

[chem. 26]

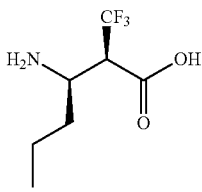

was quantitatively produced as single diastereomer (>95:5) (the relative configuration of major diastereomer was determined to be syn-body from the similarity to Example 1). The reaction-terminated liquid (prepared to be 76.1 mmol) of α-trifluoromethyl-β-substituted-β-amino acids represented by the above-mentioned formula was Celite-filtered, and the residue was washed with a small amount of methanol. To the filtrate and washing liquid, 6.3 mL (76.7 mmol, 1.01 eq) of 37% hydrochloric acid and 20 mL of water were added, and concentration under reduced pressure and drying under vacuum were made. Further, azeotropic dehydration with 40 mL of toluene was made thereby obtaining 20.0 g of hydrochloric acid salt of α-trifluoromethyl-β-substituted-β-amino acids represented by the above-mentioned formula.

To 20 mL of methanol, 2.00 g (prepared to be 7.61 mmol) of the hydrochloric acid salt and 1.61 g (8.46 mmol, 1.11 eq) of p-toluenesulfonic acid monohydrate were added, and dissolving under heating was made at 40 to 50° C., followed by making concentration under reduced pressure and drying under vacuum. To the residue, 14 mL of isopropanol and 8 mL of n-heptane were added, and then dissolving was made under heating at 90° C., followed by gradually lowering the temperature to 0° C. The precipitated crystal was filtered, and washed with a small amount of n-heptane, followed by being subjected to drying under vacuum, thereby obtaining 1.71 g of p-toluenesulfonic acid salt (refined product) of α-trifluoromethyl-β-substituted-β-amino acids represented by the above-mentioned formula. The total yield from α-trifluoromethyl-β-substituted-α,β-unsaturated esters was 60%. The diastereomer ratio was syn-body:anti-body=>98:2 according to $^1$H- and $^{19}$F-NMR analyses.

Results of $^1$H-NMR and $^{19}$F-NMR of hydrochloric acid salt and p-toluenesulfonate of α-trifluoromethyl-β-substituted-β-amino acids are shown below.

Hydrochloric acid salt of α-trifluoromethyl-β-substituted-β-amino acids:

$^1$H-NMR (reference material: internal lock, deuterated solvent: $D_2O$), δ ppm: 0.82 (t, 7.4 Hz, 3H), 1.33 (m, 2H), 1.67 (m, 2H), 3.61 (m, 1H), 3.76 (m, 1H)/$NH_2$, $CO_2H$ and HCl could not be identified; and $^{19}$F-NMR (reference material: $CF_3SO_3K$, deuterated solvent: $D_2O$), δ ppm: 13.47 (d, 9.0 Hz, 3F).

p-Toluenesulfonic acid salt of α-trifluoromethyl-β-substituted-β-amino acids:

$^1$H-NMR (reference material: internal lock, deuterated solvent: $D_2O$), δ ppm: 0.81 (t, 7.2 Hz, 3H), 1.32 (m, 2H), 1.66 (m, 2H), 2.26 (s, 3H), 3.50 (m, 1H), 3.72 (m, 1H), 7.24 (d, 8.0 Hz, 2H), 7.55 (d, 8.0 Hz, 2H)/$NH_2$, $CO_2H$ and SO3H could not be identified; and $^{19}$F-NMR (reference material: $CF_3SO_3K$, deuterated solvent: $D_2O$), δ ppm: 13.34 (d, 9.0 Hz, 3F).

The invention claimed is:

1. A process of producing a α-trifluoromethyl-β-substituted-β-amino acid represented by formula [4]

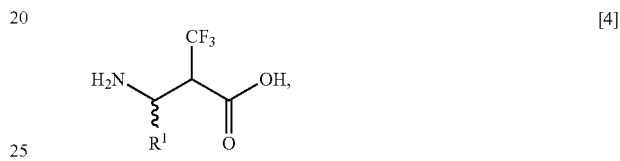

comprising:

allowing a α-trifluoromethyl-β-substituted-α,β-unsaturated ester represented by formula [1]

to react with a hydroxylamine represented by formula [2]

to convert the α-trifluoromethyl-β-substituted-α,β-unsaturated ester into a dehydrogenated closed-ring body of the α-trifluoromethyl-β-substituted-β-amino acid represented by formula [3]

to react with a hydroxylamine represented by formula [2]

to convert the α-trifluoromethyl-β-substituted-α,β-unsaturated ester into a dehydrogenated closed-ring body of the α-trifluoromethyl-β-substituted-β-amino acid represented by formula [6]

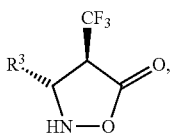

and
hydrogenolyzing the dehydrogenated closed-ring body, wherein, in the formulae,
$R^3$ is an alkyl group or a substituted alkyl group;
$R^4$ is an alkyl group;
the wavy line in formula [5] indicates that the stereochemistry of the double bond is E, Z or a mixture of E and Z;
the representation of the relative configuration in formula [6] indicates that the stereochemistry of $R^3$ to the trifluoromethyl group is anti; and

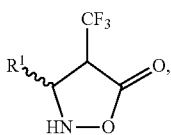

and hydrogenolyzing the dehydrogenated closed-ring body, wherein, in the formulae,
$R^1$ is an alkyl group, a substituted alkyl group, an aromatic ring group, a substituted aromatic ring group, an alkoxycarbonyl group or a substituted alkoxycarbonyl group;
$R^2$ is an alkyl group or a substituted alkyl group;
the wavy line in formula [1] indicates that the stereochemistry of the double bond is E, Z or a mixture of E and Z; and
the wavy line in formula [3] and in formula [4] indicates that the stereochemistry of $R^1$ to the trifluoromethyl group is syn, anti, or a mixture of syn and anti.

2. A process of producing a α-trifluoromethyl-β-substituted-β-amino acid represented by formula [7]

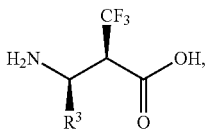

comprising:
allowing a α-trifluoromethyl-β-substituted-α,β-unsaturated ester represented by formula [5]
the representation of the relative configuration in formula [7] indicates that the stereochemistry of $R^3$ to the trifluoromethyl group is syn.

3. A dehydrogenated closed-ring body of a 60-trifluoromethyl-β-substituted-β-amino acid represented by formula [3]

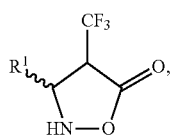

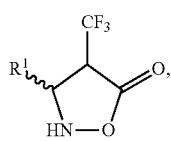

wherein
$R^1$ is an alkyl group, a substituted alkyl group, an aromatic ring group, a substituted aromatic ring group, an alkoxycarbonyl group or a substituted alkoxycarbonyl group; and
the wavy line indicates that the stereochemistry of $R^1$ to the trifluoromethyl group is syn, anti, or a mixture of syn and anti.

4. A dehydrogenated closed-ring body of a α-trifluoromethyl-β-substituted-β-amino acid represented by formula [6]

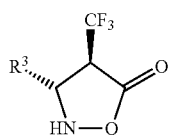

wherein
$R^3$ is an alkyl group or a substituted alkyl group; and
the representation of the relative configuration indicates that the stereochemistry of $R^3$ to the trifluoromethyl group is anti.

* * * * *